US012751752B2

(12) United States Patent
Vogt et al.

(10) Patent No.: US 12,751,752 B2
(45) Date of Patent: *Oct. 6, 2026

(54) DEVICE AND METHOD FOR PREPARING BONE CEMENT PASTE

(71) Applicant: Heraeus Medical GmbH, Wehrheim (DE)

(72) Inventors: Sebastian Vogt, Wehrheim (DE); Thomas Kluge, Wehrheim (DE)

(73) Assignee: Heraeus Medical GmbH, Wehrheim (DE)

( * ) Notice: Subject to any disclaimer, the term of this patent is extended or adjusted under 35 U.S.C. 154(b) by 757 days.

This patent is subject to a terminal disclaimer.

(21) Appl. No.: 18/319,222

(22) Filed: May 17, 2023

(65) Prior Publication Data

US 2023/0371995 A1 Nov. 23, 2023

(30) Foreign Application Priority Data

May 23, 2022 (EP) .................................... 22174728

(51) Int. Cl.
*A61B 17/88* (2006.01)

(52) U.S. Cl.
CPC .. *A61B 17/8833* (2013.01); *A61B 2017/8838* (2013.01)

(58) Field of Classification Search
CPC ............. B01F 2101/10; B01F 35/7131; A61B 17/8833
See application file for complete search history.

(56) References Cited

U.S. PATENT DOCUMENTS

| | | | |
|---|---|---|---|
| 4,671,263 A | 6/1987 | Draenert | |
| 4,973,168 A | 11/1990 | Chan | |
| 5,100,241 A | 3/1992 | Chan | |
| 5,344,232 A | 9/1994 | Nelson et al. | |
| 5,586,821 A | 12/1996 | Bonitati et al. | |
| 5,588,745 A | 12/1996 | Tanaka et al. | |
| 5,624,184 A | 4/1997 | Chan | |
| 5,997,544 A | 12/1999 | Nies et al. | |
| 6,033,105 A | 3/2000 | Barker et al. | |
| 6,709,149 B1 | 3/2004 | Tepic | |
| 9,339,317 B2 * | 5/2016 | Vogt ...................... | B01F 35/146 |

(Continued)

FOREIGN PATENT DOCUMENTS

| | | |
|---|---|---|
| DE | 3640279 A1 | 6/1987 |
| DE | 69812726 T2 | 2/2004 |

(Continued)

*Primary Examiner* — Elizabeth Insler
(74) *Attorney, Agent, or Firm* — Dicke, Billig & Czaja, PLLC

(57) ABSTRACT

A device for preparing a bone cement paste from two starting components, comprising a mixing unit comprising a hollow cylindrical cartridge with an interior, wherein a bone cement powder as a first starting component is stored in the interior, and a cartridge head which seals the interior in terms of fluid conduction at a proximal cartridge end, and a reservoir for a monomer liquid as a second starting component, comprising a conduit which connects the interior of the mixing unit to the reservoir in terms of fluid conduction, wherein the conduit extends through a cartridge head duct of the cartridge head of the mixing unit, and the conduit and the cartridge head duct form a first form closure.

15 Claims, 8 Drawing Sheets

(56) References Cited

U.S. PATENT DOCUMENTS

| | | | |
|---|---|---|---|
| 9,861,943 B2 | 1/2018 | Vogt et al. | |
| 11,109,905 B2 | 9/2021 | Vogt et al. | |
| 2017/0354942 A1* | 12/2017 | Vogt .................. | A61B 17/8827 |

FOREIGN PATENT DOCUMENTS

| | | | |
|---|---|---|---|
| DE | 102009031178 | B3 | 9/2010 |
| EP | 0380867 | B1 | 8/1997 |
| EP | 0692229 | B1 | 12/1999 |
| EP | 1005901 | A2 | 6/2000 |
| EP | 1016452 | A2 | 7/2000 |
| EP | 1020167 | A2 | 7/2000 |
| EP | 0796653 | B1 | 5/2004 |
| EP | 1886647 | A1 | 2/2008 |
| EP | 2404864 | A1 | 1/2012 |
| EP | 2578308 | A2 | 4/2013 |
| EP | 2618759 | B1 | 10/2015 |
| EP | 3150155 | A1 | 4/2017 |
| EP | 3260192 | A1 | 12/2017 |
| EP | 3838391 | A1 | 6/2021 |
| WO | 9426403 | A1 | 11/1994 |
| WO | 9967015 | A1 | 12/1999 |
| WO | 2012038002 | A1 | 3/2012 |

* cited by examiner

DEVICE AND METHOD FOR PREPARING BONE CEMENT PASTE

CROSS-REFERENCE TO RELATED APPLICATIONS

This application claims priority pursuant to 35 U.S.C. 119(a) to European Application No. 22174728.0, filed May 23, 2022, which application is incorporated herein by reference in its entirety.

FIELD

The invention is generally related to devices arranged to prepare a bone cement paste. More specifically, the present invention relates to a device for preparing a bone cement paste from two starting components, comprising a mixing unit comprising a hollow cylindrical cartridge with an interior, wherein a bone cement powder as a first starting component is stored in the interior, and a cartridge head which seals the interior in terms of fluid conduction at a proximal cartridge end, and a reservoir for a monomer liquid as a second starting component, comprising a conduit which connects the interior of the mixing unit to the reservoir in terms of fluid conduction, wherein the conduit extends through a cartridge head duct of the cartridge head of the mixing unit, and the conduit and the cartridge head duct form a first form closure. Additionally, the invention further relates to a method for preparing a bone cement paste with such a device.

BACKGROUND OF THE INVENTION

Considerable efforts are made to identify devices and methods for preparing bone cement paste, by means of which bone cement paste can be prepared simply, reliably, and quickly. An important aspect in preparing bone cement paste is the avoidance of air inclusions, for example gas bubbles, in the bone cement. To avoid this, a plurality of vacuum cementing systems have been described, of which the following are mentioned by way of example: U.S. Pat. Nos. 6,033,105 A, 5,624,184 A, 4,671,263 A, 4,973,168 A, 5,100,241 A, WO 99/67015 A1, EP 1020167 A2, U.S. Pat. No. 5,586,821 A, EP 1016452 A2, DE 3640279 A1, WO 94/26403 A1, EP 1005901 A2, EP 1886647 A1, U.S. Pat. No. 5,344,232 A.

One further development consists in the development of cementing systems in which both starting components are stored in separate regions of the mixing systems and are only mixed with one another in the cementing system immediately before the cementing application. Such closed systems, what are known as full-prepacked systems, are mentioned in the following documents: EP 0 692 229 A1, DE 10 2009 031 178 B3, U.S. Pat. Nos. 5,997,544 A, 6,709,149 B1, DE 698 12 726 T2, EP 0 796 653 A2, U.S. Pat. No. 5,588,745 A.

In WO 2012/038002 A1, a device is described in which a monomer liquid is guided via a conduit from a container into an interior of a cartridge filled with a bone cement powder, so that a bone cement paste can be prepared within the cartridge by mixing. The conduit and the cartridge are connected to one another via a form closure. After opening the container, for example by opening a valve, the monomer liquid flows via the conduit into the interior. A disadvantage of the disclosed structure of the device is that the type of opening of the container can be restricted due to the comparatively unstable connection of container to cartridge. For example, opening the container might lead to buckling of the conduit due to tilting of the ampoule.

In EP 2 404 864 A1, a device for opening ampoules, comprising an outer container, in which a closed, in terms of fluid conduction, ampoule with an ampoule body and an ampoule head is arranged, and a cavity are described, wherein the cavity comprises a connection to the ampoule and the ampoule head is arranged at least in regions in the connection. The walls of the outer container comprise at least one deformable region so that tilting of the ampoule against the connection is enabled which opens the ampoule in terms of fluid conduction.

There is a desire on the market to further simplify devices for preparing bone cement paste.

OBJECTS

It is an object of the present invention to at least partially overcome one or more of the disadvantages resulting from the prior art.

The invention is especially based on the goal of providing a device which permits simple and application-safe opening of one or more ampoules, in particular glass ampoules, with a monomer liquid for the simple, rapid, and application-safe preparation of a bone cement paste. In particular, the opening of the ampoule or ampoules should take place with as little effort as possible and with avoidance of additional separate tools. Furthermore, the opening of the ampoule with as few components as possible should be enabled. Furthermore, the monomer liquid should be provided as losslessly as possible for the preparation of the bone cement paste.

A further object of the invention is to provide a method with which bone cement can be prepared from two starting components and by means of which at least some of the objects already described are achieved at least in part.

PREFERRED EMBODIMENTS OF THE INVENTION

The features of the independent claims contribute to at least partially fulfilling at least one of the aforementioned objects. The dependent claims provide preferred embodiments which contribute to at least partially fulfilling at least one of the objects.

A first embodiment of the invention is a device for preparing a bone cement paste from two starting components, comprising

- a mixing unit comprising a hollow cylindrical cartridge with an interior, wherein a bone cement powder as a first starting component is stored in the interior, and a cartridge head which seals the interior in terms of fluid conduction at a proximal cartridge end, and
- a reservoir for a monomer liquid as a second starting component, comprising
- a conduit which connects the interior of the mixing unit to the reservoir in terms of fluid conduction, wherein the conduit extends through a cartridge head duct of the cartridge head of the mixing unit, and the conduit and the cartridge head duct form a first form closure, characterized in that

- the reservoir comprises a reservoir container, in which at least one closed, in terms of fluid conduction, ampoule with an ampoule body and an ampoule head is arranged and the monomer liquid is stored in the ampoule, and a cavity in the region of the ampoule head, wherein the cavity is connected to the conduit in terms of fluid conduction and comprises a connection to the ampoule, wherein the ampoule head is arranged at least in regions in the connection, and the reservoir container comprises a deformable region at least in portions so that tilting of the ampoule about a pivot point against the connection is enabled, wherein the connection has a connection diameter which is adapted to the dimensions of the ampoule head such that the ampoule head can be opened, in terms of fluid conduction, when the ampoule is tilted about the pivot point against the connection, and wherein the reservoir comprises a connecting element in order to connect the reservoir to the mixing unit via a second form closure.

In one embodiment of the device, the first form closure and the second form closure are reversibly detachable from the mixing unit. This embodiment is a second embodiment of the invention, which is preferably dependent upon the first embodiment of the invention.

In one embodiment of the device, in a side view, in particular a side view of the device, the pivot point, the first form closure, and the second form closure form the vertices of a triangle. This embodiment is a third embodiment of the invention, which is preferably dependent on the first or second embodiment of the invention.

In one embodiment of the device, the second form closure has a shorter distance, in particular spatial distance, from the first form closure than the pivot point. This embodiment is a fourth embodiment of the invention which is preferably dependent upon one of the preceding embodiments of the invention.

In one embodiment of the device, the first form closure, the second form closure, and the pivot point respectively lie on a straight line running parallel to a longitudinal axis of the cartridge, wherein the straight lines have a different straight-line distance, in particular spatial straight-line distance, from the longitudinal axis of the cartridge. This embodiment is a fifth embodiment of the invention, which is preferably dependent upon one of the preceding embodiments of the invention.

In one embodiment of the device, the mixing unit comprises a mixing tube which is arranged in a cartridge head passage of the cartridge head so as to be axially displaceable in the interior. This embodiment is a sixth embodiment of the invention, which is preferably dependent upon one of the preceding embodiments of the invention.

In one embodiment of the device, the second form closure is formed between the connecting element and the mixing tube. This embodiment is a seventh embodiment of the invention which is preferably dependent upon the sixth embodiment of the invention.

In one embodiment of the device, a detachable mixing rod is arranged within the mixing tube. This embodiment is an eighth embodiment of the invention which is preferably dependent on the sixth or seventh embodiment of the invention.

In one embodiment of the device, a vacuum connection is arranged on the cartridge head, via which vacuum connection the interior can be connected to a negative-pressure source, in particular a vacuum pump. This embodiment is a ninth embodiment of the invention, which is preferably dependent upon one of the preceding embodiments of the invention.

In one embodiment of the device, the conduit is a tube, a hose, or a tube and a hose, in particular a hose that is connected to a tube in terms of fluid conduction. This embodiment is a tenth embodiment of the invention, which is preferably dependent upon one of the preceding embodiments of the invention.

In one embodiment of the device, the conduit is axially displaceable in the cartridge head duct. This embodiment is an eleventh embodiment of the invention which is preferably dependent on the tenth embodiment of the invention.

In one embodiment of the device, the conduit extends at least over 70%, preferably at least over 80%, more preferably at least over 90%, of an axial interior length of the interior. This embodiment is a twelfth embodiment of the invention which is preferably dependent on the tenth or eleventh embodiment of the invention.

In one embodiment of the device, the connecting element is a clasp. This embodiment is a thirteenth embodiment of the invention, which is preferably dependent upon one of the preceding embodiments of the invention.

In one embodiment of the device, a slider is arranged on the cartridge head in order to seal, in terms of fluid conduction, the cartridge head duct after removal of the conduit from the cartridge head duct, in particular after detachment of the first form closure by removing the conduit from the cartridge head duct. This embodiment is a fourteenth embodiment of the invention, which is preferably dependent upon one of the preceding embodiments of the invention.

A fifteenth embodiment of the invention is a method for preparing a bone cement paste by means of a device according to one of the preceding embodiments of the invention, comprising the steps of:

a. opening, in terms of fluid conduction, the at least one ampoule by tilting the ampoule, stored in the reservoir container, about the pivot point against the connection,
b. flowing of the monomer liquid from the at least one ampoule into the cavity,
c. conveying the monomer liquid from the cavity into the interior via the conduit,
d. detaching the second form closure,
e. detaching the first form closure by pulling out the conduit from the cartridge head duct,
f. sealing, in terms of fluid conduction, the cartridge head duct,
g. mixing bone cement powder and monomer liquid.

GENERAL

In the present description, range specifications also include the values specified as limits. An indication of the type "in the range of X to Y" with respect to a variable A consequently means that A can assume the values X, Y and values between X and Y. Ranges delimited on one side of the type "up to Y" for a variable A accordingly mean, as a value, Y and less than Y.

Some of the described features are linked to the term "substantially." The term "substantially" is to be understood as meaning that, under real conditions and manufacturing techniques, a mathematically exact interpretation of terms such as "superimposition," "perpendicular," "diameter," or "parallelism" can never be given exactly, but only within certain manufacturing-related error tolerances. For example, "substantially parallel axes" enclose an angle of 85 degrees to 95 degrees to one another, and "substantially equal volumes" include a deviation of up to 5% by volume. A "device consisting substantially of plastic material" comprises, for example, a plastics content of ≥95 to ≤100% by weight. A "substantially complete filling of a volume B" comprises, for example, a filling of ≥95 to ≤100% by volume of the total volume of B. A "substantially complete conveying of a component C" comprises, for example, a conveying of ≥90 to ≤100% by volume, in particular ≥95 to ≤100% by volume, of the total volume of C.

The terms "proximal" and "distal" serve only to designate the spatially opposite ends of the device or of other structural units of the device and do not permit any conclusion to be drawn about the orientation with respect to a human body, for example a user of the device. "Distal to . . . " and "proximal to . . . " or similar formulations correspondingly express only the spatial arrangement of two structural units of the device in relation to one another.

DETAILED DESCRIPTION

A first subject matter of the invention relates to a device for preparing a bone cement paste from two starting components, comprising

- a mixing unit comprising a hollow cylindrical cartridge with an interior, wherein a bone cement powder as a first starting component is stored in the interior, and a cartridge head which seals the interior in terms of fluid conduction at a proximal cartridge end, and
- a reservoir for a monomer liquid as a second starting component, comprising
- a conduit which connects the interior of the mixing unit to the reservoir in terms of fluid conduction, wherein the conduit extends through a cartridge head duct of the cartridge head of the mixing unit, and the conduit and the cartridge head duct form a first form closure, characterized in that

- the reservoir comprises a reservoir container, in which at least one closed, in terms of fluid conduction, ampoule with an ampoule body and an ampoule head is arranged and the monomer liquid is stored in the ampoule, and a cavity in the region of the ampoule head,
- wherein the cavity is connected to the conduit in terms of fluid conduction and comprises a connection to the ampoule, wherein the ampoule head is arranged at least in regions in the connection, and the reservoir container comprises a deformable region at least in portions so that tilting of the ampoule about a pivot point against the connection is enabled,
- wherein the connection has a connection diameter which is adapted to the dimensions of the ampoule head such that the ampoule head can be opened, in terms of fluid conduction, when the ampoule is tilted about the pivot point against the connection, and
- wherein the reservoir comprises a connecting element in order to connect the reservoir to the mixing unit via a second form closure.

The device serves to mix a bone cement paste from a bone cement powder and a monomer liquid, wherein prior to mixing, the bone cement powder is stored in a mixing unit of the device and the monomer liquid is stored in a reservoir of the device.

The reservoir serves to store the monomer liquid before it prepares the bone cement paste by mixing with the bone cement powder in the mixing unit. For this purpose, the reservoir comprises a reservoir container for receiving a closed, in terms of fluid conduction, ampoule, in particular a glass ampoule, filled with the monomer liquid and comprising an ampoule head and an ampoule body. The reservoir container surrounds the ampoule, in particular at least the ampoule body, so that the ampoule can be stored securely in the reservoir until it is used. The reservoir container can, for example, be present in the form of a hollow cylinder into which the ampoule is inserted, wherein, for improved transport capability of the device, the reservoir container is shaped such, for example in that the reservoir container comprises a cover, that the ampoule cannot escape unintentionally from the device, in particular from the reservoir. The reservoir container is preferably shaped such that two ampoules, in particular two ampoules next to one another, can be stored, preferably with substantially parallel longitudinal axes, in the reservoir.

Furthermore, the reservoir serves to open, in terms of fluid conduction, the at least one ampoule that is closed in terms of fluid conduction. For this purpose, the reservoir comprises a cavity which is connected via a connection to the ampoule arranged in the reservoir container. The ampoule is stored in the reservoir in such a way that the ampoule head points in the direction of the cavity, whereas the ampoule body is arranged at least partially, preferably entirely, in the reservoir container. The connection extends between cavity and reservoir container, and in fact in such a way that the ampoule head is arranged at least in regions in the connection. For this purpose, the connection has a connection diameter which allows the ampoule head to be inserted into the connection at least in portions. In one embodiment, the connection has a connection diameter which allows the ampoule head to be inserted completely into the connection. The connection diameter is preferably smaller than the diameter of the ampoule body so that the latter cannot be inserted into the connection. For example, the connection is designed as a ring or hollow cylinder, and the ampoule head is surrounded at least in regions by this ring or hollow cylinder. The connection has a structural integrity which exceeds a structural integrity of the ampoule, so that the ampoule can break when it is pressed against the connection.

In order to open the ampoule or, given the presence of two or more ampoules, all ampoules, the reservoir container comprises a deformable region at least in portions, in particular adjacent to a transition of the ampoule head to the ampoule body of the ampoule. In one embodiment, the reservoir container is completely deformable. The deformable region allows tilting of the ampoule about a pivot point against the connection. The connection diameter is in this case matched to the ampoule head in such a way that, during tilting, at least the ampoule body end facing away from the ampoule head is tilted about the pivot point while at least the ampoule head end facing away from the ampoule body remains within the connection, so that the ampoule is opened in terms of fluid conduction by at least partial bursting of the ampoule, in particular in the region of an ampoule neck between ampoule head and ampoule body. The connection in this case serves primarily to fix the ampoule head against a tilting movement of the ampoule about the pivot point. For example, the connection diameter is not more than 10% larger than the diameter of the ampoule head so that a relatively slight tilting of the ampoule already leads to its opening in terms of fluid conduction.

After opening of the at least one ampoule in terms of fluid conduction, the monomer liquid can flow out of the ampoule into the cavity. The cavity is connected in terms of fluid conduction via a conduit to the mixing unit, in particular to an interior of the cartridge of the mixing unit, in which the bone cement powder is stored. Conveying of the monomer liquid from the cavity into the mixing unit via the conduit can, for example, be triggered via the force of gravity; via a negative pressure in the mixing unit, in particular in the interior of the cartridge; or a combination thereof.

The reservoir can consist of a widest variety of materials or material combinations. For example, the reservoir may consist of a polymer. The polymer is preferably a transparent polymer since, in this way, the user can visually monitor a proper functioning of the reservoir, in particular an outflow of the monomer liquid from the at least one ampoule, during use.

The mixing unit serves to mix the bone cement paste from the bone cement powder and the monomer liquid after conveying the monomer liquid into the mixing unit, in particular into the interior of the mixing unit.

The mixing unit comprises a hollow cylindrical cartridge in which the bone cement powder is stored. A hollow cylindrical cartridge is to be understood as a tubular receptacle which comprises an interior and a cartridge wall surrounding the interior. The cross section of the cartridge can assume any shape. Due to the simple manufacture and the application-safe use of the device, the cross section, and preferably also the cross section of the interior, is of circular design. This allows easy handling capability for the user and, due to the absence of edges, reduces a risk of moving parts becoming wedged within the device.

The mixing unit, in particular the cartridge, can consist of a widest variety of materials or material combinations. For example, the mixing unit, in particular the cartridge, can consist of a polymer. The polymer is preferably a transparent polymer since, in this way, the user can visually monitor a proper functioning of the mixing unit during use.

The mixing unit is connected in terms of fluid conduction to the reservoir, in particular to the cavity of the reservoir, via the conduit, which extends through a cartridge head duct of the cartridge head at the proximal cartridge end. "In terms of fluid conduction" means that liquids, in particular the monomer liquid, and gases can be exchanged between the reservoir and the mixing unit via the conduit. A filter means, in particular a pore disk, for example made of sintered polypropylene particles, of sintered or compressed polyethylene fibers, of cellulose felt, or of paperboard, is preferably arranged within the conduit, which filter means makes the conduit impermeable to solids. This prevents possible fragments of the at least one ampoule from being able to pass into the interior. The filter means is preferably arranged on the end of the conduit opposite the cavity, so that no bone cement powder can penetrate into the conduit, and the conduit can thus seal in terms of fluid conduction upon contact with the monomer liquid to form the bone cement paste. One such filter means can also be arranged in the cavity in order to already capture possible fragments of the at least one ampoule before, in spatial terms, the conduit.

The cartridge head seals the proximal cartridge end so that the bone cement powder cannot escape unintentionally from said proximal cartridge end. The cartridge head is preferably reversibly connectable to the cartridge, for example via a screw connection. At a distal cartridge end axially opposite the proximal cartridge end, a dispensing plunger is preferably arranged which can be displaced axially in the interior and seals said distal cartridge end in terms of fluid conduction. After the bone cement paste has been prepared, the bone cement paste can be discharged from the device by advancing the dispensing plunger in the direction of the proximal cartridge end. For this purpose, for example, the cartridge head at the proximal cartridge end can be removed, for example by unscrewing, or the cartridge head comprises an opening for discharging the bone cement paste.

In order to prevent an unwanted advancement of the dispensing plunger, a catch means can be arranged at the dispensing plunger so that the dispensing plunger engages with the cartridge, in particular with the cartridge wall, until the catch means is actively detached by a user of the device.

In order to prepare the bone cement paste, the mixing unit and the reservoir are connected to one another via two form closures. A first form closure is formed between the cartridge head duct of the mixing unit and the conduit of the reservoir, and a second form closure is formed between a connecting element of the reservoir and the mixing unit.

Upon opening the at least one ampoule by tilting about the pivot point against the connection, a sufficiently large force must be exerted on the ampoule in order to overcome the structural integrity of the ampoule. This force is additionally increased given use of more than one ampoule, such as preferably two ampoules, if the latter are opened simultaneously, as is preferred, by tilting about the pivot point against the connection. This force is transmitted to the contact points of reservoir and mixing unit.

If the reservoir and the mixing unit were connected only via the first form closure, the force for opening the at least one ampoule would act entirely on the conduit so that buckling or even tearing off of the conduit would occur, whereby a substantially complete conveying of the monomer liquid from the reservoir into the mixing unit, in particular the interior, would be hindered or even prevented.

The second form closure between the connecting element and the mixing unit ensures a force distribution of the force, required to open the at least one ampoule, onto the two form closures so that the risk of the device being damaged upon opening the at least one ampoule by tilting is reduced.

Via the two form closures, the reservoir is connected stably to the mixing unit in such a way that the at least one ampoule can be opened by tilting about the pivot point against the connection without damaging the device, and without requiring additional aids in addition to the device to open the at least one ampoule.

In one embodiment, the connecting element is integrally connected to the rest of the reservoir, in particular the connection, the cavity, and/or the reservoir container. In a further embodiment, the connecting means can be detachably connected to the rest of the reservoir, in particular to the connection, the cavity, and/or the reservoir container.

The two form closures may be designed such that a reversible, in particular non-destructive, separation of reservoir and mixing unit is not possible.

One embodiment of the device is characterized in that the first form closure and the second form closure are designed to be detachable from the mixing unit. This allows a simple, preferably reversible, non-destructive separation of reservoir and mixing unit so that, after conveying the monomer liquid from the at least one cartridge via the conduit into the interior of the cartridge, the reservoir can be simply separated from the mixing unit. Since the reservoir is no longer required after the conveying of the monomer liquid into the mixing unit, it can facilitate preparation of the bone cement paste for a user, for example by improved handling of the mixing unit.

The pivot point as well as the first form closure and the second form closure may be arranged spatially in different ways with respect to one another.

One embodiment of the device is characterized in that, in a side view, in particular a side view of the device, the pivot point, the first form closure, and the second form closure form the vertices of a triangle. In this embodiment, the pivot point and the two form closures lie in a common plane but are not arranged on a straight line running in this plane. The longitudinal axis of the cartridge preferably lies within this plane or runs at least parallel to this plane. The arrangement in the form of a triangle improves the force distribution of the force required for the opening of the at least one ampoule in terms of fluid conduction, in particular given a tilting movement, used for this purpose, of the ampoule about the pivot point within or parallel to the plane of the triangle. Furthermore, such an arrangement fixes and does not displace the pivot point in this plane, which facilitates a reproducible opening.

The pivot point as well as the first form closure and the second form closure may have different distances from one another.

One embodiment of the device is characterized in that the second form closure has a shorter distance from the first form closure than the pivot point. In this embodiment, the distance between pivot point and first form closure is thus greater than the distance between second form closure and first form closure. In particular given an arrangement of pivot point and the two form closures in the form of a triangle, this allows both improved force distribution of the force, required during tilting to open the ampoule, onto the two form closures and simultaneously an optimally space-saving design of the device. The latter facilitates in particular the handling of the device by a user.

The pivot point and the two form closures in this case preferably form the vertices of a triangle in a side view, wherein the pivot point and the second form closure have the smallest value of the three possible distances between the mentioned points. This leads to a further improvement of the force distribution onto the two form closures and allows a further space-saving design of the device.

One embodiment of the device is characterized in that the first form closure, the second form closure, and the pivot point respectively lie on a straight line running parallel to a longitudinal axis of the cartridge, wherein the straight lines have a different straight-line distance from the longitudinal axis of the cartridge. This arrangement improves the force distribution of the force, required during tilting to open the ampoule, onto the two form closures and also simultaneously allows an optimally space-saving design of the device. The latter facilitates in particular the handling of the device by a user.

The pivot point and the two form closures in this case preferably form the vertices of a triangle, wherein the triangle lies in a plane in which the longitudinal axis of the cartridge also lies, or to which the longitudinal axis of the cartridge runs at least in parallel.

The mixing of the bone cement powder and the monomer liquid within the mixing unit, in particular within the interior of the cartridge, may be carried out in different ways. For example, for mixing the two starting components, the device or at least the mixing unit may be shaken if the reservoir has detached from the mixing unit after the conveying of the monomer liquid from the reservoir into the mixing unit. One or more mixing balls, for example in the form of metal balls with a diameter of 1 mm to 1 cm, may in this case be provided in the interior, which mixing balls facilitate a thorough mixing of the starting components.

One embodiment of the device is characterized in that the mixing unit comprises a mixing tube which is arranged in a cartridge head passage of the cartridge head so as to be axially displaceable in the interior.

In one embodiment, a mixing element, for example in the form of a stirrer, can be introduced into the interior through the mixing tube from outside the device, in order to mix the starting components after the monomer liquid has been conveyed through the conduit into the interior. For example, a mixing element can be inserted into the mixing tube so far that the mixing element protrudes from the mixing tube into the interior and the starting components are mixed by repeated axial up-and-down movement of the mixing tube with the mixing element in the cartridge head passage. In a preferred embodiment, the mixing tube itself comprises a mixing element in order to mix the starting components by repeated axial up-and-down movement of the mixing tube in the cartridge head passage. A mixing disk is in this case preferably arranged on a mixing tube end facing toward the dispensing plunger.

After mixing of the starting components has taken place and, if necessary, after the removal of the mixing rod from the mixing tube, the mixing tube can be used as a dispensing spout for the controlled delivery of the bone cement paste from the device. For this purpose, the mixing tube is preferably pulled axially as far as possible out of the cartridge head passage and then fixed within said cartridge head passage with the cartridge head, for example by means of a screw thread.

One embodiment of the device is characterized in that a detachable mixing rod for improved mixing of the starting components within the interior is arranged within the mixing tube. The mixing rod can represent a mixing element which extends axially through the mixing tube and is fixedly connected to the mixing tube for mixing of the starting components. For this purpose, the mixing rod preferably comprises a mixing element on a mixing rod end facing toward the dispensing plunger.

If the mixing tube itself already comprises a mixing element, the mixing rod serves for the facilitated operation of the mixing tube. In addition, the mixing rod improves handling of the device and reduces the risk of the mixing tube buckling during mixing of the starting components. Furthermore, the mixing rod seals the mixing tube in terms of fluid conduction and thus prevents the starting components, which, within the mixing rod, are not accessible to a thorough mixing via the mixing tube, from accumulating within said mixing tube.

At a mixing rod end opposite the dispensing plunger, the mixing rod preferably comprises a handle in order to reversibly move the mixing rod, together with the mixing tube connected thereto, axially up and down in the interior in order to mix the starting components.

The mixing rod is preferably detachably connected to the mixing tube via the handle so that the mixing rod can be pulled out of the mixing tube by removing the handle. As a result, after the preparation of the bone cement paste, the mixing tube can be used as a dispensing spout for the bone cement paste. For this purpose, the mixing tube is preferably pulled out of the cartridge head passage as far as possible and then fixedly connected to the cartridge head in the cartridge head passage so that the mixing tube is no longer axially movable. This may preferably occur via a screw thread.

The second form closure between the reservoir, in particular between the connecting element of the reservoir, and the mixing unit can take place at different points of the mixing unit.

One embodiment of the device is characterized in that the second form closure is formed between the connecting element and the mixing tube. This facilitates an attachment of the reservoir to the side of the cartridge head opposite the interior, and thus facilitates a conveying of the monomer liquid through the conduit into the interior. The latter is in particular facilitated if utilizing the force of gravity for conveying the monomer liquid. In addition, such an arrangement of the second form closure allows an optimally simple and space-saving design of the device.

One embodiment of the device is characterized in that a vacuum connection is arranged on the cartridge head, via which vacuum connection the interior can be connected in terms of fluid conduction to a negative-pressure source, for example a vacuum pump. The vacuum connection thus allows application of a negative pressure in the interior, which negative pressure may, for example, be used to convey the monomer liquid from the reservoir, in particular from the cavity of the reservoir, through the conduit into the interior. This allows simple and rapid conveying of the monomer liquid into the interior. Furthermore, the negative pressure in the interior can be applied or maintained during the mixing of the bone cement paste from the two starting components. Air inclusions in the bone cement paste, which could have a disadvantageous effect on the cured bone cement, can thereby be reduced or avoided.

The conduit can be designed differently in order to conduct the monomer liquid into the interior of the cartridge of the mixing unit.

One embodiment of the device is characterized in that the conduit is a tube, a hose, or a combination of a tube and a hose. This allows a simple production as well as easy and space-saving arrangement of the conduit within the interior. The conduit is preferably a tube.

It is preferred that the conduit, in particular in the form of a tube and/or a hose, has a fluid-conducting internal conduit diameter in a range of 0.5 mm to 2 mm, preferably in a range of 0.5 mm to 1.5 mm. Smaller diameters slow the conveying of the monomer liquid. Due to smaller capillary effects in the conduit, larger diameters hinder a substantially complete conveying of the monomer liquid.

One embodiment of the device is characterized in that the conduit is axially displaceable in the cartridge head duct, preferably in the interior of the cartridge. This allows simple detachment of the first form closure by pulling the conduit out of the cartridge head duct. The cartridge head duct preferably surrounds the conduit in a collar-like manner, wherein the conduit is preferably a tube. This represents a stable first form closure which can be detached in a controlled and simple manner by pulling the conduit out of the cartridge head duct. In order to facilitate detachment of the first form closure by pulling out the conduit from the cartridge head duct, it is more preferred that the conduit is a flexible tube.

The conduit extends in or through the cartridge head duct and can extend, in particular axially, to different extents into the interior of the cartridge. In one embodiment, the conduit extends through the cartridge head duct and terminates flush therewith on the side of the interior. In this embodiment, the conduit does not extend within the interior.

One embodiment of the device is characterized in that the conduit extends at least over 70%, preferably at least over 80%, more preferably at least over 90% of an axial interior length of the interior. Given spatial orientation of the device with the proximal cartridge end upward and correspondingly the distal cartridge end downward, so that bone cement powder is stored in the vicinity of the distal cartridge end, this allows conveying of the monomer liquid directly into the bone cement powder which is stored in the interior and preferably does not fill the entire interior of the cartridge but rather, for example, only 20-70% by volume of the entire volume of the interior. In this respect, it is preferred that the amount of bone cement powder is selected such that, in the vertical orientation of the cartridge with the cartridge head upward, the conduit can guide the monomer liquid at least onto a surface of the bone cement powder, preferably at least 1 cm deep into the bone cement powder. This facilitates mixing of the starting components of the bone cement paste. Furthermore, the monomer liquid is thereby released in the spatial vicinity of the distal cartridge end in the interior, and thus at a comparatively large spatial distance from the vacuum connection on the cartridge head, if present. It is thereby prevented that when negative pressure is applied to the vacuum connection, the monomer liquid is sucked into the vacuum connection and is thus not available for mixing with the bone cement powder.

The connecting element can be designed differently in order to form the second form closure between reservoir and mixing unit.

One embodiment of the device is characterized in that the connecting element is a clasp. The clasp is preferably formed from two clasp notches on a reservoir outer surface, for example an outer surface of the reservoir container, of the cavity or of the connection and from a reversibly detachable clasp element, wherein the clasp element comprises two protuberances which can be inserted into the two clasp notches so that the clasp surrounds the mixing unit, preferably the mixing tube of the mixing unit, in a collar-like manner and thus forms the first form closure. This allows a fast and simply designed and detachable first form closure which is stable and allows safe opening of the at least one ampoule by tilting about the pivot point.

One embodiment of the device is characterized in that a slider is arranged on the cartridge head in order to seal the cartridge head duct in terms of fluid conduction after removal of the conduit from the cartridge head duct, preferably by pulling the conduit out of the cartridge head duct.

Mixing of the bone cement from the starting components within the mixing unit is thereby enabled, in particular in the interior of the cartridge, with applied negative pressure at the vacuum connection. Air inclusions in the bone cement paste, which could have a disadvantageous effect on the cured bone cement, can thereby be reduced or avoided.

A further subject matter of the invention relates to methods for preparing a bone cement paste from two starting components by means of an embodiment of the device described above, comprising the steps of:

a. opening, in terms of fluid conduction, the at least one ampoule by tilting the ampoule, stored in the reservoir container, about the pivot point against the connection,
b. flowing of the monomer liquid from the at least one ampoule into the cavity,
c. conveying the monomer liquid from the cavity into the interior via the conduit,
d. detaching the second form closure,
e. detaching the first form closure by pulling out the conduit from the cartridge head duct,
f. sealing, in terms of fluid conduction, the cartridge head duct,
g. mixing bone cement powder and monomer liquid.

In a step a., the at least one ampoule, wherein one or two ampoules are preferred, can be opened in terms of fluid conduction by tilting the ampoule, stored in the reservoir container, about the pivot point against the connection. The tilting is enabled by the region of the reservoir container that is deformable, at least in portions. The at least one ampoule is stored in the reservoir in such a way that the ampoule head is arranged at least in regions in the connection of the reservoir so that, during tilting of the ampoule, in particular of the ampoule body in the reservoir container, about the pivot point, the ampoule head is pressed against the connection and its structural integrity is thus overcome so that the monomer liquid can flow out of the at least one ampoule.

Upon opening, the ampoule preferably breaks in the region of the ampoule neck between ampoule head and ampoule body.

In a step b., the monomer liquid flows from the ampoule opened in step a. into the cavity of the reservoir. In order to facilitate the flow out of the ampoule, the device is preferably held such that the at least one ampoule assumes an angle in a range of 15-35° to the surface of the earth. Depending on the embodiment of the diameter of the connection, the ampoule head can fall into the cavity of the reservoir upon opening the ampoule in step a. The cavity is preferably dimensioned such that the ampoule head can be completely accommodated in the cavity and the ampoule head is additionally rotatable in the cavity. Monomer liquid possibly present in the ampoule head can thus flow out into the cavity due to the force of gravity and is thus available for preparing the bone cement paste.

In a step c., the monomer liquid is conveyed from the cavity into the interior via the conduit. In one embodiment of the method, the force of gravity is utilized to convey the monomer liquid into the interior. In a further, preferred embodiment of the method, the conveying is triggered by a negative pressure in the interior, wherein it is preferred that the negative pressure in the interior is generated by applying a negative pressure, for example via connection, in terms of fluid conduction, of the vacuum connection on the cartridge head to a negative-pressure source, for example a vacuum pump. In this embodiment, the monomer liquid is preferably introduced directly into the bone cement powder by means of the conduit so that a suction of the monomer liquid from the interior through vacuum connection and into the negative-pressure source is avoided.

After the monomer liquid has been conveyed into the mixing unit, there is no longer need to keep the reservoir connected to the mixing unit via the two form closures.

In a step d., the second form closure between the connecting element and the mixing unit, preferably between the connecting element and the mixing tube of the mixing unit, is detached.

In a step e., the first form closure is detached by pulling the conduit out of the cartridge head duct.

Steps d. and e. may be performed in any order, wherein it is preferred to perform first step d. and then step e. since pulling out the conduit in step e. is facilitated if the second form closure has already been detached.

In a step f., the cartridge head duct is sealed in terms of fluid conduction after the conduit has been pulled out, so that the bone cement paste can be mixed given applied negative pressure. The sealing of the cartridge head duct in terms of fluid conduction preferably takes place by actuating the slider.

In a step g., mixing of the bone cement powder and the monomer liquid takes place to prepare the bone cement paste. The mixing preferably takes place with applied negative pressure in the interior. The mixing more preferably takes place under up-and-down movement of the mixing tube to actuate the mixing rod in the mixing tube.

The prepared bone cement paste may be discharged from the device in different ways. For example, the bone cement paste may be retrieved from the interior with a spatula.

One embodiment of the method is characterized in that, after the mixing of the bone cement paste, the mixing rod used for this purpose is detached from the mixing tube and removed therefrom by pulling so that the mixed bone cement paste is discharged from the interior through the mixing tube out of the device by advancing the dispensing plunger in the direction of the cartridge head. This reduces the work steps of the user that are necessary for discharging the bone cement paste, and the tools necessary for this purpose.

In order to dispense the bone cement paste from the device, the device is preferably connected to a dispensing aid, in particular a dispensing gun, which displaces the dispensing plunger in the direction of the cartridge head and thus expels the bone cement paste from the interior.

The device is characterized in that it prepares a bone cement paste from two starting components. A bone cement paste is understood to mean a substance that is suitable in the field of medical technology for creating a stable connection between artificial joints, such as hip and knee joints, and bone material. By curing, a bone cement paste becomes a bone cement. These bone cements are preferably polymethyl methacrylate bone cements (PMMA bone cements). PMMA bone cements have been used for a long time in medical applications and are based on the work of Sir Charnley (cf. Charnley, J., Anchorage of the femoral head prosthesis of the shaft of the femur. *J. Bone Joint Surg.* 1960; 42, 28-30). In this respect, PMMA bone cements may be produced from a bone cement powder as a first starting component and a monomer liquid as a second starting component. With a suitable composition, the two starting components can be storage-stable, separately from one another. When the two starting components are brought into contact with one another, a plastically-deformable bone cement paste is produced by the swelling of the polymer components of the bone cement powder. In this case, polymerization of the monomer by radicals is initiated. As the polymerization of the monomer progresses, the viscosity of the bone cement paste increases until it cures completely.

Bone cement powder is understood to mean a powder that comprises at least one particulate polymethyl methacrylate and/or a particulate polymethyl methacrylate copolymer. Examples of copolymers are styrene and/or methyl acrylate. In one embodiment, the bone cement powder can additionally comprise a hydrophilic additive which supports the distribution of the monomer liquid within the bone cement powder. In a further embodiment, the bone cement powder can additionally comprise an initiator which initiates the polymerization. In a further embodiment, the bone cement powder can additionally comprise a radiopaque material. In yet a further embodiment, the bone cement powder can additionally comprise pharmaceutically active substances, such as antibiotics.

The bone cement powder preferably comprises, as a hydrophilic additive, at least one particulate polymethyl methacrylate and/or a particulate polymethyl methacrylate copolymer, an initiator, and a radiopaque material, or consists of these components. More preferably, the bone cement powder comprises at least one particulate polymethyl methacrylate and/or a particulate polymethyl methacrylate copolymer, an initiator, a radiopaque material, and a hydrophilic additive, or consists of these components. Most preferably, the bone cement powder comprises at least one particulate polymethyl methacrylate and/or a particulate polymethyl methacrylate copolymer, an initiator, a radiopaque material, a hydrophilic additive, and an antibiotic, or consists of these components.

According to the invention, the particle size of the particulate polymethyl methacrylate and/or of the particulate polymethyl methacrylate copolymer of the bone cement powder can correspond to the sieve fraction of less than 150 μm, preferably less than 100 μm.

According to the invention, the hydrophilic additive can be designed in particulate and/or fibrous form. In a further embodiment, the hydrophilic additive can be slightly soluble, and preferably insoluble, in methyl methacrylate. In a further embodiment, the hydrophilic additive can have an absorption capacity of at least 0.6 g methyl methacrylate per gram of hydrophilic additive. In a further embodiment, the hydrophilic additive can comprise a chemical substance comprising at least one OH group. In this case, it can preferably be provided that the hydrophilic additive has covalently bonded OH groups at its surface. Examples of such preferred hydrophilic additives can be additives selected from the group comprising cellulose, oxycellulose, starch, titanium dioxide, and silicon dioxide, wherein pyrogenic silicon dioxide is particularly preferred. In one embodiment, the particle size of the hydrophilic additive can correspond to the sieve fraction of less than 100 μm, preferably less than 50 μm, and most preferably less than 10 μm. The hydrophilic additive can be contained in an amount of 0.1 to 2.5% by weight, based on the total weight of the bone cement powder.

According to the invention, the initiator can contain dibenzoyl peroxide or consist of dibenzoyl peroxide.

According to the invention, a radiopaque material is understood to mean a substance that allows the bone cement to be made visible on diagnostic X-ray images. Examples of radiopaque materials can include barium sulfate, zirconium dioxide, and calcium carbonate.

According to the invention, the pharmaceutically active substance can comprise one or more antibiotics and, optionally, added cofactors for the one or more antibiotics. Preferably, the pharmaceutically active substance consists of one or more antibiotics and, optionally, added cofactors for the one or more antibiotics. Examples of antibiotics include, inter alia, gentamicin, clindamycin, and vancomycin.

According to the invention, the monomer liquid can comprise the monomer methyl methacrylate or consist of methyl methacrylate. In one embodiment, the monomer liquid comprises, in addition to the monomer, an activator dissolved therein, such as N,N-dimethyl-p-toluidine, or consists of methyl methacrylate and N,N-dimethyl-p-toluidine.

The features disclosed for the device are also disclosed for the method, and vice versa.

FIGURES

In the following, the invention is illustrated further, by way of example, by figures. The invention is not limited to the figures.

Shown are:

FIG. 1 a schematic longitudinal section of a device for preparing a bone cement paste, comprising a mixing unit and a reservoir with two ampoules filled with a monomer liquid, FIG. 2 a perspective side view of a portion of the device of FIG. 1, FIG. 3 the device of FIGS. 1 and 2, wherein a first form closure, a second form closure, and a pivot point are indicated, FIG. 4 the device of FIGS. 1 to 3 given a fluid-conducting opening of the two ampoules, FIG. 5 the device of FIGS. 1 to 4 during conveying of the monomer liquid into the mixing unit, FIG. 6 the device of FIGS. 1 to 5, wherein the reservoir is separated from the mixing unit and the bone cement paste is prepared in the mixing unit, FIG. 7 the device of FIGS. 1 to 6 during discharging of the bone cement paste from the mixing unit, and FIG. 8 a flow chart of a method for preparing a bone cement paste.

Figure 1:
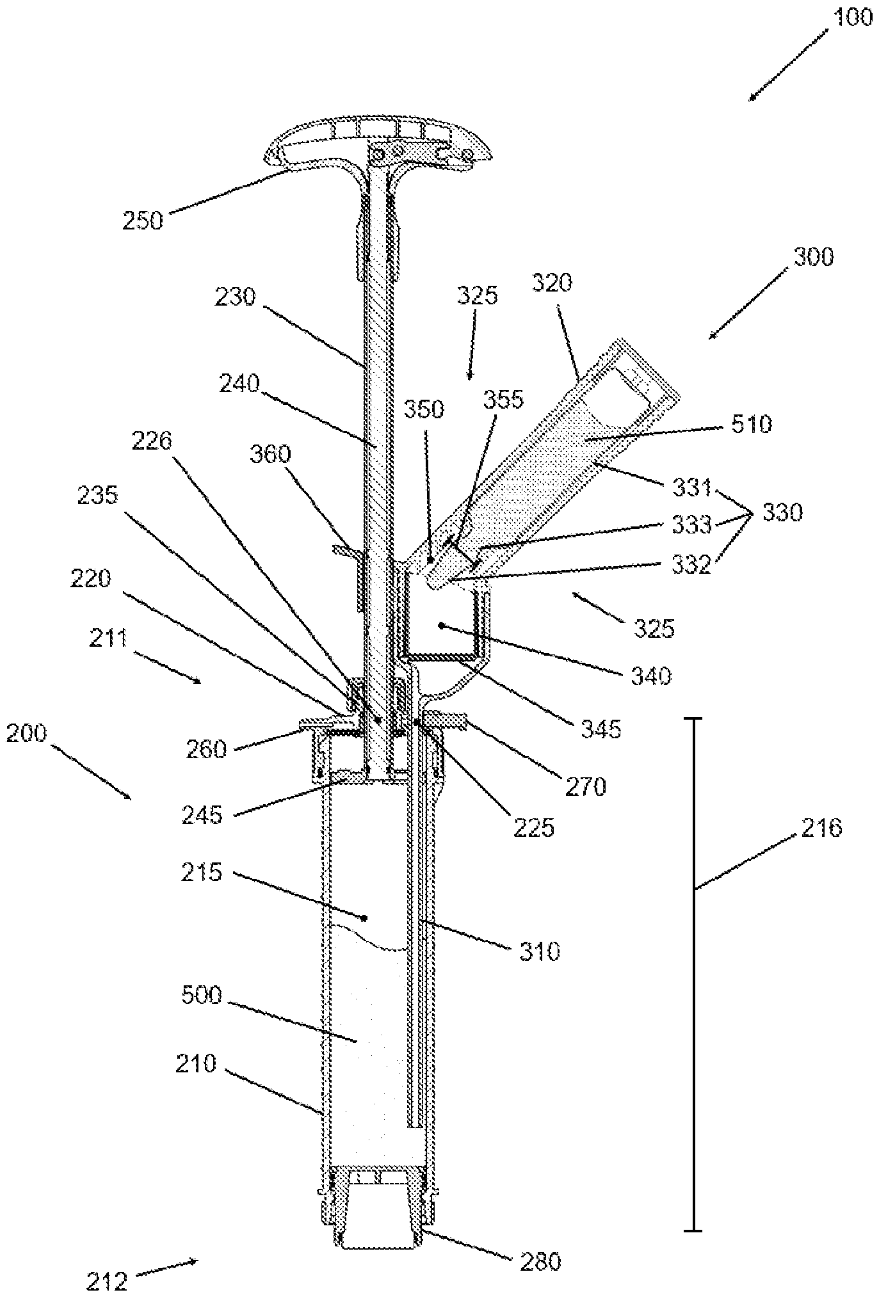
FIG. 1 shows a schematic longitudinal section of a side view of an exemplary embodiment of a device 100 for preparing a bone cement paste from two starting components, in an initial state. The device 100 comprises a mixing unit 200 and a reservoir 300, which are connected to one another via two form closures (see also FIG. 3).

The mixing unit 200 is constructed like a tube and comprises a hollow cylindrical cartridge 210 with an interior 215, in which a bone cement powder 500 is stored as a first starting component. A proximal cartridge end 211 of the cartridge 210 is sealed in terms of fluid conduction with a reversibly detachable cartridge head 220, and a distal cartridge end 212 axially opposite the proximal cartridge end 211 is sealed in terms of fluid conduction with a dispensing piston 280 that can be displaced axially in the interior 215. In the shown embodiment of the device 100, the cartridge 210 and the cartridge head 220 are constructed from two components. In further embodiments (not shown), the cartridge 210 and the cartridge head 220 can be designed in one piece.

The cartridge head 220 comprises a cartridge head passage 226 through which a mixing tube 230 is introduced into the interior 215 so as to be axially movable. A screw thread 235 on the cartridge head 220 can fix the mixing tube 230 by means of a screwing movement such that the mixing tube 210 is no longer axially displaceable in the interior 215. Arranged within the mixing tube 230 is a mixing rod 240 which is detachably fastened to the mixing tube 230 via a detachable handle 250 at a proximal mixing tube end and is thus movable axially in the interior 215 together with the mixing tube 230. The handle 250 serves for simplified handling of the device 100 by a user in that it facilitates an axial movement of the mixing tube 230 together with the mixing rod 240 within the interior 215. At a distal mixing tube end facing toward the dispensing piston 280, the mixing tube 230 is equipped with a mixing element 245 in the form of a mixing disk which facilitates mixing of the bone cement paste in the interior 215 via an axial displacement of the mixing tube 230 within the interior 215.

A vacuum connection 260, formed like a tube, is attached to the cartridge head 220, via which vacuum connection the interior 215 can be connected in terms of fluid conduction to a negative-pressure source (not shown).

The reservoir 300 comprises a tubular reservoir container 320 in which two ampoules 330 are stored next to one another (only one of the ampoules 330 is visible in the shown view; the second ampoule 330 is stored next to the shown ampoule 330, behind the drawing plane). The ampoules 330 comprise an ampoule body 331, an ampoule head 332 facing toward the mixing unit 200, and an ampoule neck 333, which lies between ampoule body 331 and ampoule head 332 and acts as a predetermined breaking point for the ampoules 330. A monomer liquid 510 is stored in the ampoules 330 as a second starting component of the bone cement paste. The ampoule heads 332 of the ampoules 330 are arranged in portions in a connection 350 which connects a cavity 340 of the reservoir 300 to the ampoules 330. The connection 350 has a connection diameter 355 which is approximately 5% larger than a diameter of the ampoule heads, so that the connection 350 is fixed to the ampoule heads 332 against tilting within the drawing plane. The reservoir container 320 comprises a deformable region 325 in the region of a transition from connection 350 to ampoule body 331 in order to enable tilting of the ampoules 330, in particular of the ampoule heads 332, against the connection 350, wherein, in the shown embodiment, tilting is possible in the drawing plane.

Within the cavity 340, a filter element 345 is arranged in the reservoir 300 so that after the ampoules 330 have been opened in terms of fluid connection, fragments thereof cannot pass via the cavity 340 into the mixing unit 200 but rather are retained on the filter element 345.

The cavity 340 is connected in terms of fluid conduction via a conduit 310, in the form of a tube, to the interior 215 of the cartridge 210. For this purpose, the conduit 310 extends into the interior 215 via a cartridge head duct 225 of the cartridge head 220. The conduit extends approximately over 80% of an interior length 216 of the interior 215 so that, given the shown orientation of the device 100, the monomer liquid 510 can be conveyed directly into the bone cement powder 500 via the conduit 310 and has a sufficiently large distance from the vacuum connection 260 of the mixing unit so that the risk of the monomer liquid 510 being suctioned out of the conduit 310 via the vacuum connection 260 from the interior 215 is reduced.

The cartridge head duct 225 and the conduit 310 form a first form closure (cf. also FIG. 3) by which the mixing unit 200 and the reservoir 300 are connected to one another.

The reservoir 300 furthermore comprises a connecting element 360 in the form of a clasp (cf. also FIG. 2) which is arranged in a collar-like manner around the mixing tube 310 and forms a second form closure (cf. also FIG. 3) between mixing unit 200 and reservoir 300.

Arranged on the cartridge head 220 is a slider 270 which, after removal of the conduit 310 from the cartridge head duct 225, makes it possible to seal the cartridge head duct 225 in terms of fluid conduction via a displacement in the direction of the mixing tube 230.

Figure 2:
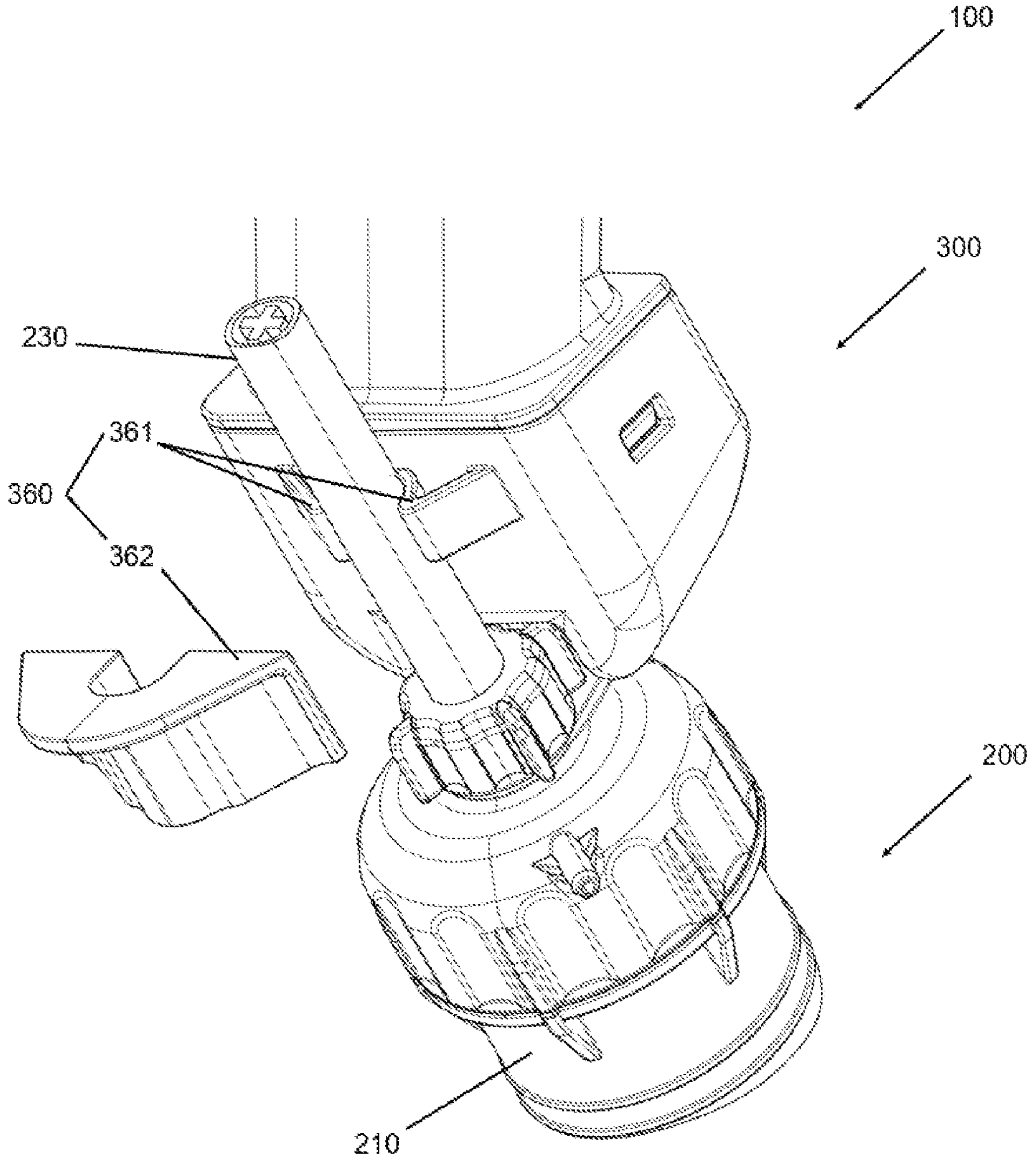

FIG. 2 shows a schematic side view of a portion of the device 100 of FIG. 1. It is visible in FIG. 2 that the connecting element 360 is formed from two clasp notches 361 on an outer surface of the reservoir 300 and a clasp element 362 that can be detached from the two clasp notches 361. The clasp element comprises two protuberances (not shown) which can be inserted into the two clasp notches 261 so that the connecting element 360 can be reversibly closed in a collar-like manner around the mixing tube 230 in order to form the second form closure stably and securely between the mixing unit 200 and the reservoir 300. In the shown embodiment, the two clasp notches 361 and the two protuberances of the clasp element 362 are of triangular design, wherein an outer diameter of the protuberances substantially corresponds to a respective internal diameter of the clasp notches 261.

Figure 3:
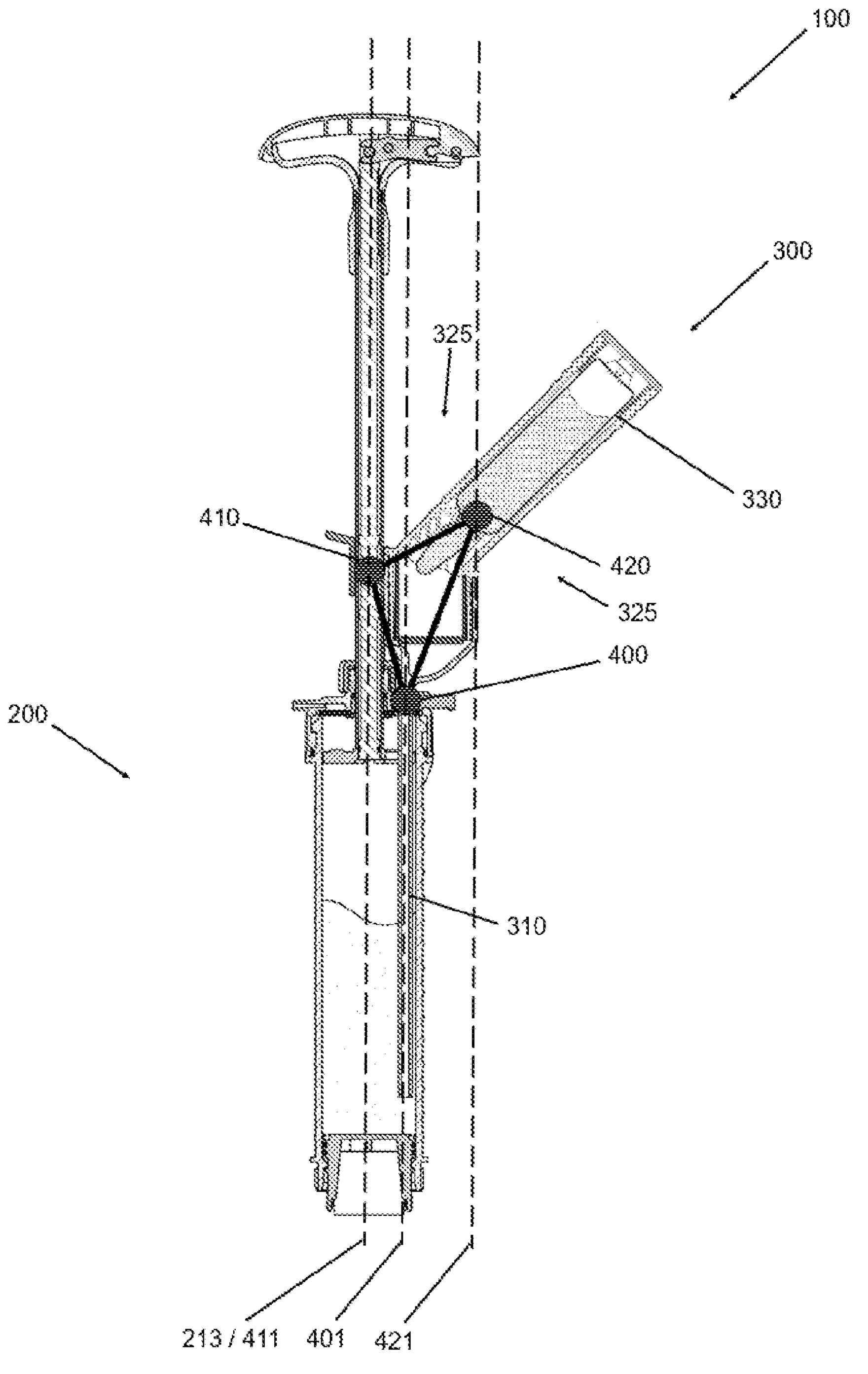

FIG. 3 shows the device 100 of FIGS. 1 and 2, wherein the first form closure 400, the second form closure 410, and a pivot point 420 about which, due to the deformable region 325, the ampoules 330 can be pressed by tilting against the connection (cf. FIG. 1) are indicated by filled circles.

In the shown side view of the device 100, the first form closure 400, the second form closure 410, and the pivot point 420 form a triangle (indicated by connecting lines between the filled circles). When the ampoules 330 are tilted about the pivot point 420 so that the ampoules 330, in particular the ampoule heads 332 (cf. FIG. 1), are pressed against the connection 350 (cf. FIG. 1), the force required in this case for the opening of the ampoules 330 in terms of fluid conduction is distributed to the first form closure 400 and the second form closure 410. An advantageous force distribution is achieved via the arrangement of the first form closure 400, the second form closure 410, and the pivot point 420 in the form of a triangle. In particular, the risk of the conduit 310 buckling or breaking off can thereby be reduced.

The first form closure 400, the second form closure 410, and the pivot point 420 are arranged relative to one another in such a way that the second form closure 410 has a shorter distance from the first form closure 400 than the pivot point 420. The pivot point 420 and the first form closure 400 are thus spaced farther apart from one another than the first form closure 400 and the second form closure 410. This ensures improved force distribution of the force, required during tilting about the pivot point 420 to open the ampoules 330, onto the two form closures 400, 410 and also, at the same time, ensures an optimally space-saving design of the device 100. The latter in particular facilitates the handling of the device 100 by a user.

The first form closure 400 lies on a straight line 401 running parallel to a longitudinal axis 213 of the cartridge 210, the second form closure 410 lies on a further straight line 411 running parallel to the longitudinal axis 213 of the cartridge 210, wherein the longitudinal axis 213 and the straight line 411 through the second form closure 410 are substantially congruent, and the pivot point lies on a further straight line 421 lying parallel to the longitudinal axis 213 of the cartridge 210, wherein the straight lines 401, 411, 421 all have a different straight-line distance from the longitudinal axis 213 of the cartridge 210. In the shown embodiment, the straight-line distance between the straight line 421 through the pivot point and the longitudinal axis 213 is greatest, followed by the straight-line distance between the straight line 401 through the first form closure 400, and the longitudinal axis 213. The different straight-line distances improve the force distribution of the force, required during tilting about the pivot point 420 to open the ampoules 330, onto the two form closures 400, 410, and at the same time allow an optimally space-saving design of the device 100. The latter in particular facilitates the handling of the device 100 by a user.

Figure 4:
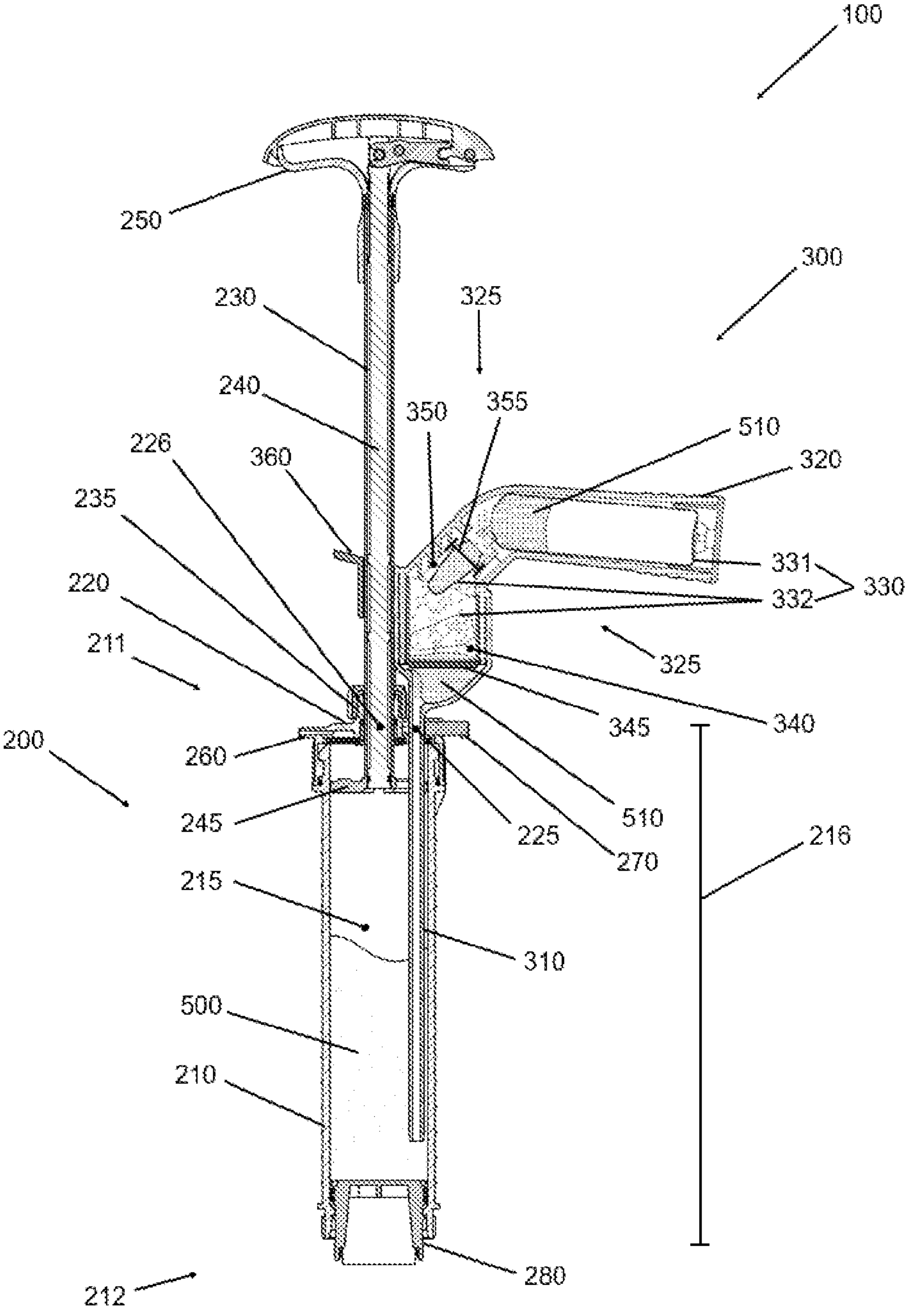

FIG. 4 shows the device 100 of FIGS. 1 to 3 with ampoules 330 tilted about the pivot point 420 (cf. FIG. 3). For this purpose, the reservoir container 320 was bent at the deformable region 325 so that the ampoule heads 332 were pressed against the connection 250 and the ampoules 330 were opened in terms of fluid conduction in the region of the ampoule necks (cf. FIG. 1). The monomer liquid 510 stored in the ampoules 330 opened in terms of fluid conduction has already partially flowed out of the ampoules 330 into the cavity 340. One of the two ampoule heads 332 is still arranged in portions in the connection 350, while the other of the two ampoule heads 332 has completely passed from the connection 350 into the cavity 3350. The ampoule head 332 that has passed completely into the cavity 340 was captured by the filter element 345 so that said ampoule head or fragments thereof cannot pass to or through the conduit 310. The cavity 340 is dimensioned in such a way that the ampoule heads 332 can be stored so as to be completely rotatable therein, so that monomer liquid 510 that is possibly still present in the ampoule head 332 after the opening of the ampoules 330 can flow out into the cavity 340. This has already occurred in FIG. 4, given the ampoule head 332 arranged completely in the cavity 340. In the shown embodiment of the device 100, the conduit, in particular a diameter of the conduit, is designed such that, due to its surface tension, the monomer liquid 510 cannot flow through the conduit 310 into the interior 215 of the cartridge 210 solely due to the force of gravity. The monomer liquid 510 flowed out of the ampoules 330 therefore collects in the cavity 340 until a user of the device 100 actively intervenes.

Figure 5:
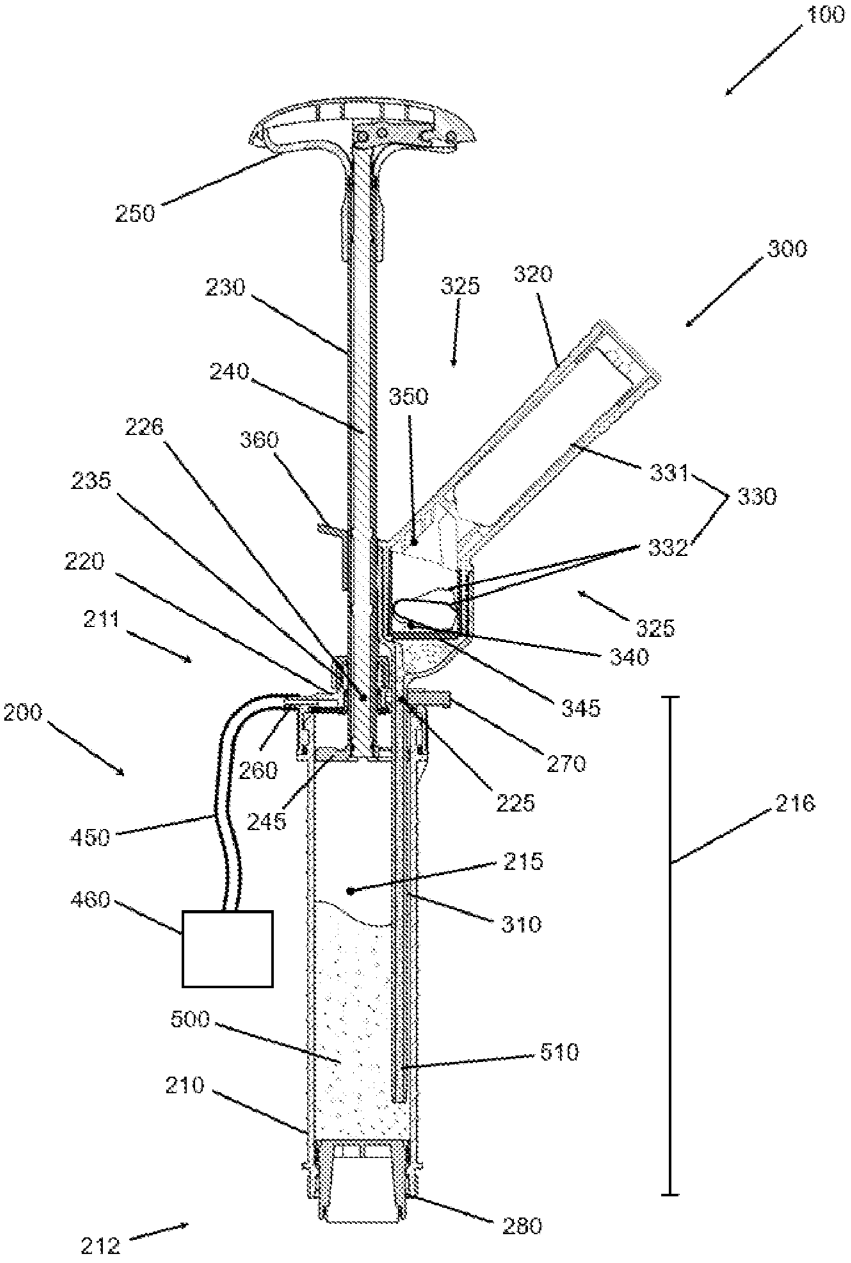

FIG. 5 shows the device 100 of FIGS. 1 to 4 during conveying of the monomer liquid 510 from the reservoir 300, in particular from the cavity 340 of the reservoir 300, into the interior 215 of the cartridge 210 of the mixing unit 200. The monomer liquid 510 has flowed substantially completely from the ampoules 330. In order to convey the monomer liquid 510 through the conduit 310, the vacuum connection 260 has been connected in terms of fluid conduction via a hose 450 to a negative-pressure source 460 in the form of a vacuum pump. Given an active negative-pressure source 460, this generates a negative pressure in the interior 215 and draws the monomer liquid 510 from the reservoir 300 into the mixing unit 200. Due to the axial extension of the conduit 310, the monomer liquid 510 is introduced directly into the bone cement powder 500, which reduces the risk of said monomer liquid being sucked through the vacuum connection 260 into the negative-pressure source 460. The negative pressure in the interior 215 is maintained at least until the monomer liquid 510 is substantially completely transferred into the mixing unit 200.

Figure 6:
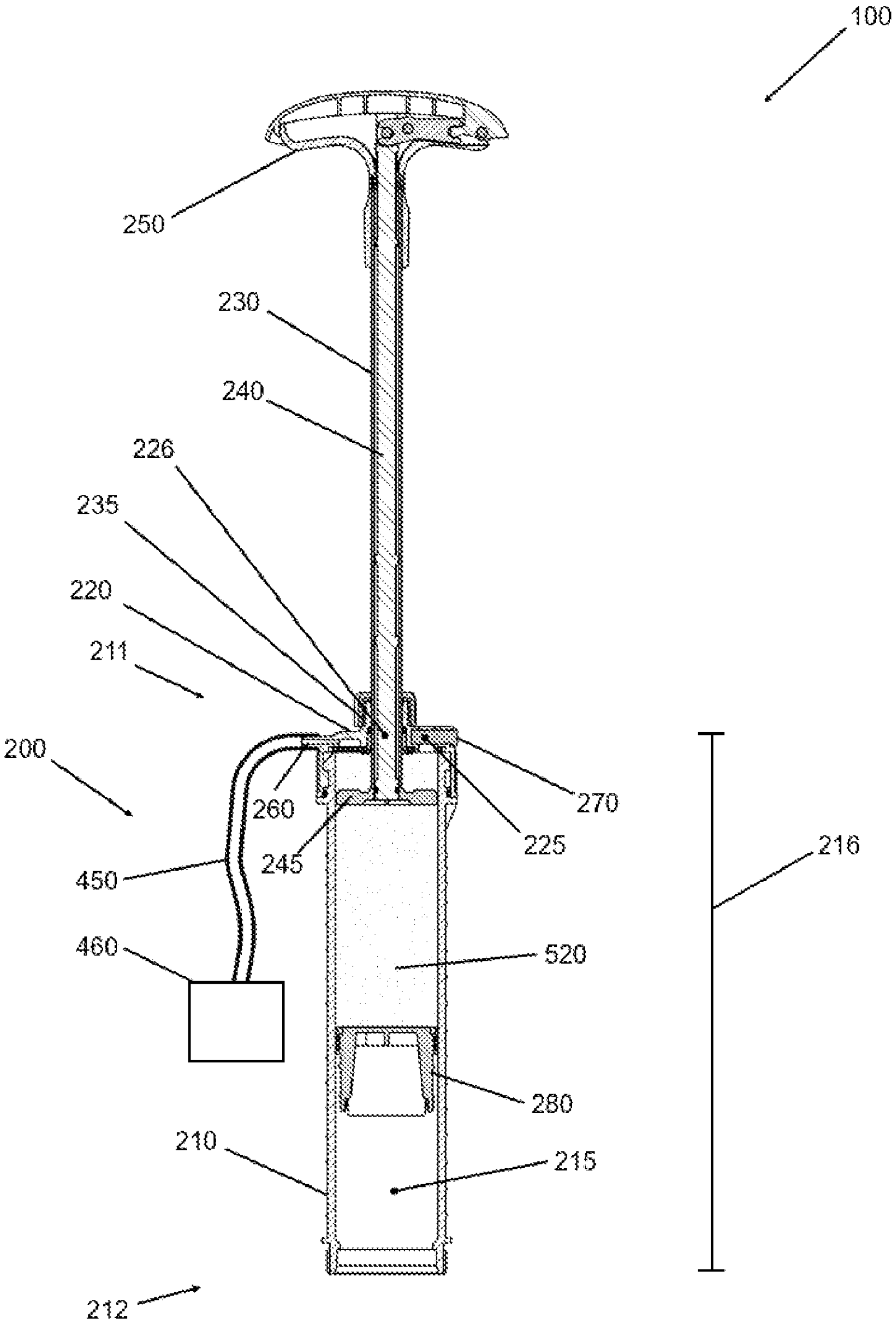

FIG. 6 shows the device 100 of FIGS. 1 to 5 with bone cement paste 520 prepared in the interior 215 and with reservoir 300 removed. In order to remove the reservoir 300, the first form closure 400 and the second form closure 410 between mixing unit 200 and reservoir 300 were detached (cf. FIGS. 1 to 5). In order to detach the second form closure 410, the clasp element 362 has been pulled out of the two clasp notches 261 (cf. FIG. 2), and in order to detach the first form closure 400, the conduit 310 has been pulled out of the cartridge head duct 225 (cf. FIGS. 1 to 5). Due to simpler handling, first the second form closure 410 and then the first form closure 400 (cf. FIG. 3) were detached. After removal of the reservoir 300, the cartridge head duct 225 was sealed in terms of fluid conduction by inserting the slider 270, so that the mixing of the bone cement paste 520 can take place with negative pressure applied in the interior 215.

In order to mix the starting components to prepare the bone cement paste 520, the mixing tube 230 together with the mixing element 245 was repeatedly axially moved up and down in the interior 215.

After the preparation of the bone cement paste 520, the previously fixed dispensing plunger 280 was detached so that the negative pressure of the negative-pressure source 460 acting in the interior 215 displaces the dispensing plunger 280 in the direction of the cartridge head 220. This allows collection of the bone cement paste 520 in the region of the cartridge head 220, which facilitates later dispensing of said bone cement paste from the device 100.

Figure 7:
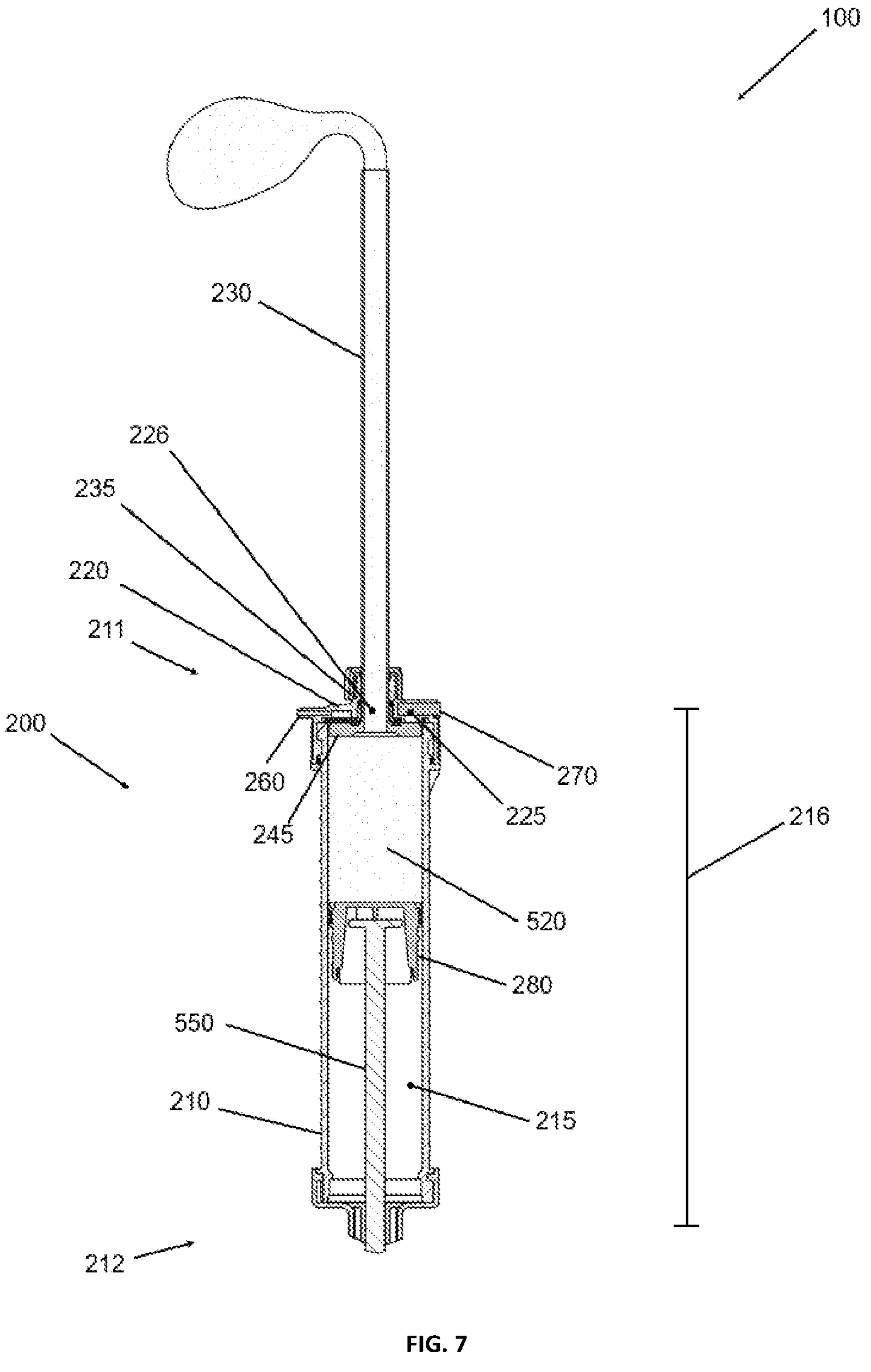

FIG. 7 shows the device 100 of FIGS. 1 to 6 during discharging of the bone cement paste 520. For this purpose, the mixing tube 230 was pulled out of the interior 215, through the cartridge head passage 226 until the mixing element 245 rests distally against the cartridge head 220. Furthermore, the detachable handle 250 together with the mixing rod 240 was removed from the mixing tube 230 (cf. FIGS. 1 to 6).

After removal of the mixing rod 240 from the mixing tube 230 (cf. FIGS. 1 to 6), the mixing tube 230 can serve as a fluid-conducting dispensing spout for the prepared bone cement paste 520. So that the mixing tube 230 is not unintentionally pushed back into the interior 215 during the discharging of the bone cement paste 520, it is reversibly fixed in the cartridge head passage 226 with the screw thread 235.

The bone cement paste 520 is dispensed from the device 100 by advancing the dispensing plunger 280 in the direction of the cartridge head 220. In order to facilitate the dispensing of the bone cement paste 520 for the user, the advancement of the dispensing plunger 280 happens with the aid of a dispensing aid 550 in the form of a dispensing gun (only partially shown).

Figure 8:
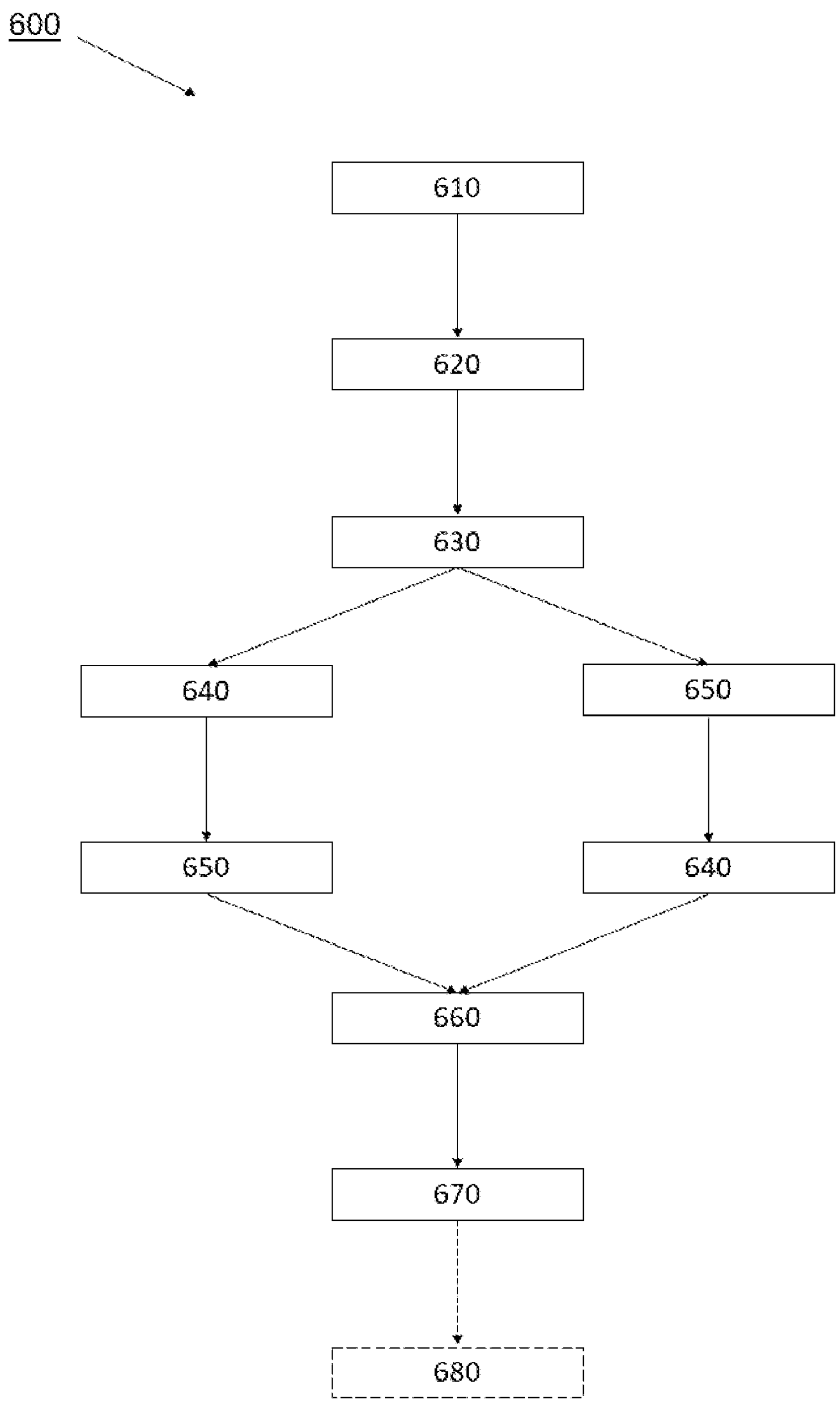

FIG. 8 shows a flow chart of a method 600 for preparing a bone cement paste 520 from two starting components by means of a device 100 according to FIGS. 1 to 7, comprising steps 610 to 670 and preferably also step 680.

In a step 610, the at least one ampoule 330 in the reservoir 300 is opened in terms of fluid conduction by tilting about the pivot point 420 against the connection 350. The force required for this purpose is distributed onto the two form closures 400, 410 so that buckling of the conduit 310 is prevented.

In a step 620, the monomer liquid 510 flows from the at least one ampoule 330, opened in terms of fluid conduction in step 610, into the cavity 340 of the reservoir 300. The outflow of the monomer liquid 510 is preferably caused by the force of gravity. During the outflow of the monomer liquid 510, the ampoule head 332, further or other fragments of the at least one ampoule 332 are preferably retained by a filter element 345 in the cavity 340 so that it or they cannot penetrate into the conduit 310.

In a step 630, the monomer liquid 510 is conveyed from the cavity 340 via the conduit 310 into the interior 215 of the cartridge 210 and to the bone cement powder 500. In one embodiment, the force of gravity is utilized to convey the monomer liquid 510. In a further embodiment, a negative pressure applied in the interior 215 is used to convey the monomer liquid 510, which negative pressure is preferably provided via a negative-pressure source 460, for example a vacuum pump, connected to the vacuum connection 260. The conveying of the monomer liquid 510 preferably takes place directly into the bone cement powder 500, which can bring about a better mixing capability and, at the same time, reduces or prevents a risk of the monomer liquid 510 being sucked from the interior 215 via the vacuum connection 260 when negative pressure is applied.

In a step 640, detachment of the second form closure 410 takes place. The connecting element 360 is preferably a clasp so that the clasp element 362 is pulled out of the two clasp notches 361 to detach the second form closure 410.

In a step 650, detachment of the first form closure 400 takes place by pulling the conduit 310 out of the cartridge head duct 225.

By detaching 640, 650 the two form closures 400, 410, the reservoir 300 is separated from the mixing unit 200 and can be removed. This facilitates the handling of the mixing unit 200.

The two form closures 400, 410 can be detached in any order or even simultaneously. In a first alternative, step 640 takes place chronologically before step 650. In a second alternative, step 650 takes place chronologically before step 640.

Since the conduit 310 is preferably designed as a tube which extends in the interior 215 at least over 70% of the axial interior length 216 of the interior 215, the first alternative is preferred for reasons of simpler handling.

In a step 660, sealing of the cartridge head duct 225 in terms of fluid conduction takes place, in particular chronologically after the removal of the conduit 310 in step 650. This allows mixing of the bone cement powder 500 and monomer liquid 510 under negative pressure, which can reduce air inclusions in the bone cement paste 520.

The cartridge head duct 225 is preferably sealed by means of a slider 270.

In a step 670, a mixing of bone cement powder 500 and monomer liquid 510 takes place in the interior 215 of the cartridge 210 of the mixing unit 200. For this purpose, it is preferred that when negative pressure is applied, in the monomer liquid 510 is mixed with the bone cement powder 500 by means of the mixing rod 230 to form the bone cement paste 520. The mixing rod 240 is preferably detachably connected to the mixing tube 230 so that an axial movement of the mixing rod 240 is transmitted directly to the mixing tube 230. The mixing tube 230 is preferably equipped with the mixing element 245, preferably in the form of a mixing disk, in order to facilitate mixing. By mixing with applied negative pressure, air inclusions are reduced in the prepared bone cement paste 520.

In order to apply the prepared bone cement paste 520 from the device 100 at a desired location, it is preferred that, in an optional step 680, the mixing rod 240 is detached from the mixing tube 230, preferably by removing the handle 250, and is pulled out of the mixing tube 230. Preferably, before or after the removal of the mixing rod 240 from the mixing tube 230, the mixing tube 230 is pulled out of the cartridge head passage 226 so far that the mixing tube 230 can be used as a dispensing spout for the bone cement paste 520. By advancing the dispensing plunger 280 in the direction of the cartridge head 220, the bone cement paste 520 is discharged from the device 100 through the mixing tube 230. The advancement of the dispensing plunger 280 in the direction of the cartridge head 220 is preferably triggered with the aid of a dispensing aid 550, for example a dispensing gun. This facilitates the use of the device 100 by the user.

REFERENCE SIGNS

100 Device
200 Mixing unit
210 Hollow cylindrical cartridge
211 Proximal cartridge end
212 Distal cartridge end
213 Longitudinal axis of the cartridge
215 Interior of the cartridge
216 Interior length
220 Cartridge head
225 Cartridge head duct
226 Cartridge head passage
230 Mixing tube
235 Screw thread
240 Mixing rod
245 Mixing element
250 Handle
260 Vacuum connection
270 Slider
280 Dispensing plunger
300 Reservoir
310 Conduit
320 Reservoir container
325 Deformable region
330 Ampoule
331 Ampoule body
332 Ampoule head
333 Ampoule neck
340 Cavity
345 Filter element
350 Connection
355 Connection diameter
360 Connecting element
361 Clasp notches
362 Clasp element
400 First form closure
401 Straight line through first form closure
410 Second form closure
411 Straight line through second form closure
420 Pivot point
421 Straight line through pivot point
450 Hose
460 Negative-pressure source
500 Bone cement powder
510 Monomer liquid
520 Bone cement paste
550 Dispensing aid
600 Method
610 Opening in terms of fluid conduction
620 Flowing
630 Conveying
640 Detaching of second form closure
650 Detaching of first form closure
660 Sealing in terms of fluid conduction
670 Mixing
680 Dispensing

What is claimed is:

1. A device for preparing a bone cement paste from two starting components, comprising:

a mixing unit comprising a hollow cylindrical cartridge with an interior, wherein a bone cement powder as a first starting component is stored in the interior, and a cartridge head which seals the interior in terms of fluid conduction at a proximal cartridge end, and a reservoir for a monomer liquid as a second starting component, comprising a conduit connecting the interior of the mixing unit to the reservoir in terms of fluid conduction, wherein the conduit extends through a cartridge head duct of the cartridge head of the mixing unit, and the conduit and the cartridge head duct form a first form closure, wherein the reservoir comprises a reservoir container, in which at least one closed, in terms of fluid conduction, ampoule with an ampoule body and an ampoule head is arranged and the monomer liquid is stored in the ampoule, and a cavity in the region of the ampoule head, wherein the cavity is connected to the conduit in terms of fluid conduction and comprises a connection to the ampoule, wherein the ampoule head is arranged at least in regions within the connection, and the reservoir container comprises a deformable region at least in portions so that tilting of the ampoule about a pivot point against the connection is enabled, wherein the connection has a connection diameter which is adapted to the dimensions of the ampoule head such that the ampoule head can be opened, in terms of fluid conduction, when the ampoule is tilted about the pivot point against the connection, and wherein the reservoir comprises a connecting element to connect the reservoir to the mixing unit via a second form closure.

2. The device according to claim 1, wherein the first form closure and the second form closure are designed so as to be reversibly detachable from the mixing unit.

3. The device according to claim 1, wherein the pivot point, the first form closure, and the second form closure form the vertices of a triangle in a side view.

4. The device according to claim 1, wherein the second form closure has a shorter distance from the first form closure than the pivot point.

5. The device according to claim 1, wherein the first form closure, the second form closure, and the pivot point respectively lie on a straight line running parallel to a longitudinal axis of the cartridge, wherein the straight lines have a different straight-line distance from the longitudinal axis of the cartridge.

6. The device according to claim 1, wherein the mixing unit comprises a mixing tube arranged in a cartridge head passage of the cartridge head so as to be axially displaceable within the interior.

7. The device according to claim 6, wherein the second form closure is formed between the connecting element and the mixing tube.

8. The device according to claim 6, wherein a detachable mixing rod is arranged within the mixing tube.

9. The device according to claim 1, wherein a vacuum connection is arranged on the cartridge head, via which vacuum connection the interior can be connected, in terms of fluid conduction, to a negative-pressure source.

10. The device according to claim 1, wherein the conduit is a tube and/or a hose.

11. The device according to claim 10, wherein the conduit is axially displaceable in the cartridge head duct.

12. The device according to claim 10, wherein the conduit extends at least over 70% of an axial interior length of the interior.

13. The device according to claim 1, wherein the connecting element is a clasp.

14. The device according to claim 1, wherein a slider is arranged on the cartridge head in order to seal the cartridge head duct in terms of fluid conduction after removal of the conduit from the cartridge head duct.

15. A method for preparing a bone cement paste from two starting components by means of a device according to claim 1, comprising the steps of:

a. opening, in terms of fluid conduction, the at least one ampoule by tilting the ampoule, stored in the reservoir container, about the pivot point against the connection,
b. flowing of the monomer liquid from the at least one ampoule into the cavity,
c. conveying the monomer liquid from the cavity into the interior via the conduit,
d. detaching the second form closure,
e. detaching the first form closure by pulling the conduit out of the cartridge head duct,
f. sealing, in terms of fluid conduction, the cartridge head duct,
g. mixing bone cement powder and monomer liquid.

* * * * *